United States Patent [19]

Descamps et al.

[11] Patent Number: 4,816,598

[45] Date of Patent: Mar. 28, 1989

[54] 4-AMINO-BUTANOIC ACID DERIVATIVES

[75] Inventors: Marcel Descamps, Wavre; Walter Verstraeten, Mechlin, both of Belgium

[73] Assignee: Sanofi, France

[21] Appl. No.: 62,612

[22] Filed: Jun. 16, 1987

Related U.S. Application Data

[63] Continuation of Ser. No. 735,684, May 20, 1985, abandoned.

[30] Foreign Application Priority Data

Jun. 6, 1984 [FR] France ............... 84 08868

[51] Int. Cl.$^4$ .................. C07C 101/30; C07C 101/34
[52] U.S. Cl. .................... 560/157; 548/479; 560/12; 560/22; 560/24; 560/29; 560/32; 560/38; 560/39; 560/115; 560/121; 560/123; 560/124; 560/125; 560/160; 560/163; 560/170
[58] Field of Search ............ 560/39, 170, 12, 22, 560/38, 115, 121, 123, 124, 125, 24, 29, 32, 157, 160, 163; 548/479

[56] References Cited

PUBLICATIONS

March; J., *Advanced Organic Chemistry*, McGraw-Hill, N.Y., 1968, p. 692.
Stevlmann; R. et al., *Liebigs Ann. Chem.*, 1975, 2245-2250.
Brewster; R., *Organic Chemistry*, Prentice-Hall, N.Y., 1948, pp. 596-597.
Albert; A. et al., *Ionization Constants of Acids and Bases*, Methuen, London, 1962, pp. 128-131.
McOmie; J. (Editor), *Protective Groups in Organic Chemistry*, Plenum, London, 1973, p. 43.
Vogel; A., *Textbook of Practical Organic Chemistry*, 3rd Ed., pp. 1095 and 1097.

*Primary Examiner*—Richard A. Schwartz
*Attorney, Agent, or Firm*—Bacon & Thomas

[57] ABSTRACT

The invention relates to 4-amino-butanoic acid derivatives of general formula:

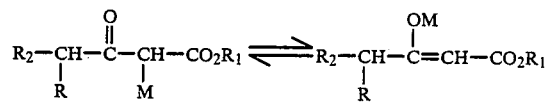

in which:

M represents an alkali metal atom,
R represents a protected amino group,
$R_1$ represents a labile group,
$R_2$ represents hydrogen, a branched- or straight-chain alkyl radical having from 1 to 6 carbon atoms, a lower methyloxyalkyl, a lower methylthioalkyl, a lower (lower alkyl)-aminoalkyl, a lower di-(lower alkyl)-aminoalkyl or a lower hydroxyalkyl radical or $R_2$ represents one of the radicals of general formulae:

Cy—A—, Cy—O—A'—, R—A'— or $R_3$S—A'— in which:

Cy represents an aromatic or alicyclic hydrocarbon radical or heterocyclic radical having one oxygen or sulphur atom or one or two nitrogen atoms, Cy being optionally mono-, di- or tri-substituted by radicals comprising hydroxy, lower alkyl, lower alkoxy, trifluoromethyl, nitro or halogeno radicals,
A represents a single bond or a branched- or straight-chain alkylene radical having from 1 to 5 carbon atoms,
A' represents a branched- or straight-chain alkylene radical having from 1 to 5 carbon atoms,
$R_3$ represents a S-protecting group.

These compounds are useful as intermediate products more particularly for the final synthesis of (3S,4S)-3-hydroxy-4-amino-6-methyl-heptanoic acid or statine.

18 Claims, No Drawings

4-AMINO-BUTANOIC ACID DERIVATIVES

This application is a continuation of application Ser. No. 735,684 filed May 20, 1985 now abandoned.

This invention relates to novel 4-amino-butanoic acid derivatives of general formula:

$$R_2-\underset{R}{\underset{|}{CH}}-\overset{O}{\overset{\|}{C}}-\underset{M}{\underset{|}{CH}}-CO_2R_1 \rightleftharpoons R_2-\underset{R}{\underset{|}{CH}}-\overset{OM}{\overset{|}{C}}=CH-CO_2R_1$$

I                                          I' in which:
M represents an alkali metal atom for instance lithium, sodium or potassium,
R represents a protected amino group,
$R_1$ represents a labile group,
$R_2$ represents hydrogen, a branched- or straight-chain alkyl radical having from 1 to 6 carbon atoms such as methyl, ethyl, n-propyl, isopropyl, n-butyl, isobutyl, tert-butyl, 1-methyl-propyl, n-pentyl or n-hexyl, a lower methyloxyalkyl radical such as methyloxyethyl, a lower methylthioalkyl radical such as methylthiomethyl, a lower (lower alkyl)-aminoalkyl radical such as methylamino-,ethylamino-, isopropylamino- or tert-butylaminoethyl, a lower di-(lower alkyl)- aminoalkyl radical such as dimethylamino-, diethylamino-, di-n-propyl- amino- or di-n-butylamino-ethyl, a lower hydroxyalkyl radical such as hydroxymethyl or 1-hydroxyethyl or $R_2$ represents one of the radicals of general formulae:

Cy—A—, Cy—O—A'—, R—A'— or $R_3$S—A'— in which:
Cy represents an aromatic or alicyclic hydrocarbon radical or heterocyclic radical having one oxygen or sulphur atom or one or two nitrogen atoms, Cy being optionally mono-, di- or tri-substituted by radicals comprising hydroxy, lower alkyl lower alkoxy trifluoromethyl, nitro- or halogeno-radicals,
A represents a single bond or a branched- or straight-chain alkylene radical having from 1 to 5 carbon atoms,
A' represents a branched- or straight-chain alkylene radical having from 1 to 5 carbon atoms,
$R_3$ represents a S-protecting group.

In the present context, the terms set out below have the meanings indicated: "protected amino group" designates a phthalimido group, an amino group protected by a proton or by an easily removable protecting group for amino groups such as, for example, an alkylcarbonyl group such as fomryl, acetyl or propionyl, an alkoxycarbonyl group such as tert-butoxycarbonyl, an alkoxyalkylcarbonylgroup such as methoxyacetyl or methoxypropionyl, a substituted alkoxycarbonyl group such as 2,2,2-trichloroethoxycarbonyl, an aralkyloxy-carbonyl group such as benzyloxycarbonyl, a substituted aralkyloxycarbonyl group such as p-nitrobenzyloxycarbonyl, a trityl, methoxytrityl or an arylsulfonyl group such as p-toluenesulfonyl. The tert-butoxycarbonyl (BOC) group constitutes a preferred group. "lower alkyl" designates saturated aliphatic hydrocarbon radicals having up to 4 carbon atoms such as methyl, ethyl, n-propyl, isopropyl, n-butyl, isobutyl or tert-butyl. "lower alkoxy" designates the hydroxy group substituted by a lower alkyl radical as defined above. "labile group" designates an easily removable esterifying group such as a lower alkyl radical as defined above or a substituted or unsubstituted aralkyl group such as benzyl or xylyl. "aromatic or alicyclic hydrocarbon radical" means a phenyl, naphthyl, cycloalkyl from 3 to 7 carbon atoms such as a cyclopropyl, cyclobutyl, cyclopentyl, cyclohexyl or cycloheptyl radical. "heterocyclic radical" means a furyl, benzofuryl, thienyl, benzothienyl, pyrrolyl, pyridil, piperidyl, morpholyl, piperazinyl, N-(lower alkyl)-piperazinyl, indolyl or 1H-imidazolyl radical. "S-protecting group" designates an easily removable protecting group for mercapto groups such as, for example, an aralkyl group such as benzyl, a substituted aralkyl group such as p-nitrobenzyl, a substituted alkoxycarbonyl group such as 2,2,2-trichloro-ethoxycarbonyl, an aralkylthioalkyl group such as benzylthiomethyl, a substituted aralkyloxycarbonyl group such as p-methoxybenzyloxycarbonyl, a picolyl group such as γ-picolyl, an alkylcarbamoyl group such as ethylcarbamoyl, an alkoxyalkylcarbamoyl group such as methoxymethylcarbamoyl, an alkanecarboxamidoalkyl group such as methanecarboxamidomethyl, a diarylalkyl group such as diphenylmethyl, a heterocyclic oxygenated group such as dihydropyranyl or tetrahydrofuranyl or a trityl group.

Thus, taking the above-cited meanings into account:
the radical Cy-A- can more particularly represent a phenyl or hydroxyphenyl radical such as 4-hydroxyphenyl, a methylphenyl, mono-fluoro-, mono-chloro- or mono-bromo-phenyl, a di-fluoro-, di-chloro- or di-bromophenyl, a mono-methoxy, di-methoxy or tri-methoxy-phenyl, a trifluoromethylphenyl, nitrophenyl, benzyl,phenethyl, cyclohexyl, cyclohexylnethyl, picolyl, piperidinomethyl ,indolylmethyl such as 3-indolylmethyl or a 1H-imidazolylmethyl such as 1H-imidazol-4-yl-methyl, the radical Cy—O—A'—can represent more particularly a phenoxyethyl or phenoxy-n-propyl radical,
the radical R—A'—can more particularly represent a N-protected 4-aminobutyl radical,
the radical $R_3$S—A'— can more particularly represent an S-protected mercaptomethyl radical.

Representative compounds of the present invention are those of formula I—I' in which R has the meaning given above, and in particular —NHBOC, $R_1$ has the same meaning as above and more particularly methyl or ethyl, M has the same meaning as above and more particularly sodium and $R_2$ represents a methyl, ethyl, n-propyl, isopropyl, n-butyl, isobutyl, phenyl, p-hydroxyphenyl, benzyl, cyclohexyl, cyclohexylmethyl, 3-indolyl-methyl or 1H-imidazol-4-yl-methyl.

The compounds of formula I—I' wherein R, $R_1$ and M have the same meaning as above and $R_2$ represents isobutyl are regarded as preferred ccmpounds of the invention, particularly methyl(4S)-3-oxo-4-N-BOC-amino-6-methy-heptanoate, ethyl(4S)-3-oxo-4-N-BOC-amino-6-methyl-heptanoate, n-propyl(4S)-3-oxo-4-N-BOC-amino-6-methyl-heptanoate, isopropyl(4S)-3-oxo-4-N-BOC-amino-6-methyl-heptanoate, n-butyl(4S)-3-oxo-4-N-BOC-amino-6-methyl-heptanoate, isobutyl (4S)-3-oxo-4-N-BOC-amino-6-methyl-heptanoate, tert-butyl(4S)-3-oxo-4-N-BOC-amino-6-methyl-heptanoate and benzyl(4S)-3-oxo-N-BOC-amino-6-methyl-heptanoate.

The compounds of the invention have been found particularly useful as intermediate products in particular for the final synthesis of (3S,4S)-3-hydroxy-4-aminobutanoic acid derivatives of general formula:

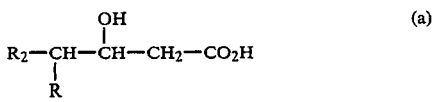

wherein R and $R_2$ have the same meaning as above and more particularly for the final synthesis of (3S,4S)-3-hydroxy-4-amino-6-methyl-heptanoic acid or statine.

A first object of the invention relates, therefore, to the 4-amino-10 butanoic acid derivatives of formula I—I' as novel industrial products useful, particularly, as intermediates for example for the final synthesis of the acids of formula (a) above and in particular for the final synthesis of statine.

For reasons of facility, the nomenclature adopted hereinafter is based on the β-ketonic form of the compounds of the invention represented by formula I.

Peptides deriving from analogs of 4-amino-butanoic acid and more particularly from statine are already known. These peptides are useful tial antihypertensive agents acting by inhibiting the enzyme which transforms renin into angiotensin. Such compounds, resembling pepstatin, are described for instance in U.S. Pat. No. 4,485,099 or in European patent application No. 104,964.

The synthesis of peptides of this kind requires an easy process for obtaining the acids of formula (a) and more particularly for obtaining statine through compounds with reacting functions protected by labile groups.

In the particular case of statine, such compounds can be, for example, alkyl esters of (3S,4S)-3-hydroxy-4-N-BOC-amino-6-methyl-heptanoic acid such as the methyl ester [Bull. Soc. Chim. France, No. 7–8, pp. 230–232 (1983)] or the ethyl ester (Liebigs Ann. Chem., 1975, p. 2245).

A process is cited in this latter reference for the preparation of a mixture of two diastereoisomers of ethyl 3-hydroxy-4-N-BOC-amino-6-methyl-heptanoate namely the (3S,4S) and (3R,4S) isomers which process involves, as one of the intermediate products, ethyl (4S)-3-oxo-4-N-BOC-amino-6-methyl-heptanoate.

However, the separation of the mixture of isomers so obtained has not been carried out.

According to the process described, ethyl (4S)-3-oxo-4-N-BOC-amino-6-methyl-heptanoate was prepared from the magnesium enolate of ethyl acid malonate which was condensed in an ether with N-BOC-L-leucine imidazolide.

The ethyl heptanoate derivative so obtained was in oily form crystallizing only after several weeks. Furthermore, the yield obtained after purification by fractional crystallization was low being about 36.6%.

Hydrogenation of this ethyl ester was then carried out providing a mixture of ethyl(3S,4S; 3R,4S)-3-hydroxy-4-N-BOC-amino-6-methyl-heptanoate in a yield of 32.5% calculated from the N-BOC-L-leucine.

Likewise, a process similar to that described above has been disclosed in Eur. J. Med. Chem., 1978, 13, No. 5, pp. 429–434 by which ethyl(4R) or (4S)-3-oxo-4-N-BOC-amino-pentanoate is hydrogenated to provide a mixture, apparently neither purified nor separated, of (3S,4S; 3R,4S)-3-hydroxy-4-N-BOC-amino-pentanoate in a yield not higher than 50% calculated from the (+)-BOC-D-alanine or (−)-BOC-L-alanine.

It has been found, within the framework of the present invention, that the alkali metal salts of formula I—I' constitute intermediate products which are particularly valuable for preparing mixtures of esters of the corresponding N-protected (3S,4S; 3R,4S)-3-hydroxy-4-amino-butanoic acid derivatives and, in particular, for preparing mixtures of the corresponding lower alkyl N-protected (3S,4S; 3R,4S)-3-hydroxy-4-amino-6-methyl-heptanoates since these salts can provide these compounds with a high degree of purity snd in yields far superior to those obtained by the technique of the prior art.

These mixtures can be easily separated into their diastereoisomers to provide the desired (3S,4S) isomer in particularly pure form. For instance, the preparation of mixtures of isomers of lower alkyl 3-hydroxy-4-amino-6-methyl-heptanoates can be carried out from compounds of formula I—I' above in which R represents BOC—NH— and $R_2$ represents isobutyl.

In this manner, a yield of at least 55% can be obtained calculated from the N-BOC-L-leucine.

Amongst the (3S,4S) isomers of lower alkvl 3-hydroxy-4-N-BOC-amino-6-methyl-heptanoate referred to above, the (3S,4S) isomer of methyl 3-hydroxy-4-N-BOC-amino-6-methyl-heptanoate is in crystalline form which is particularly useful. Therefore, the compounds of formula I—I' which are capable of providing this isomer can be regarded as preferred compounds of the invention, namely the compounds of formula I—I' in which R represents the BOC-NH-radical, $R_1$ represents the methyl radical, $R_2$ represents the isobutyl radical and M represents sodium.

The 4-amino-butanoic acid derivatives of the invention can be prepared from an N-protected imidazolide of general formula:

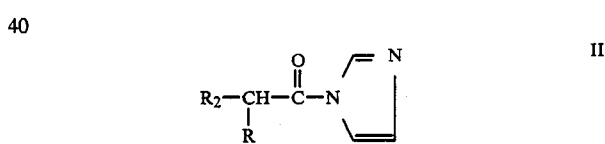

in which R and $R_2$ have the same meaning as above.

This imidazolide of formula II is first reacted with a magnesium enolate of a malonic acid monoester of general formula:

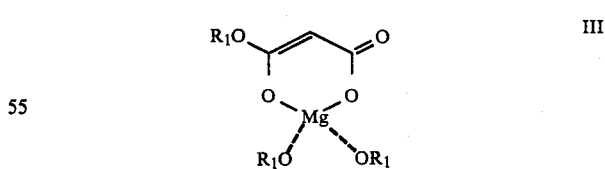

wherein $R_1$ has the same meaning as above, the reaction taking place at room-temperature and in an ether such as tetrahydrofuran, optionally in the presence of an aprotic solvent such as dimethylsulphoxide or N,N-dimethylformamide, to give a complex which is hydrolysed in the presence of a strong acid, for example hydrochloric acid, so as to provide the esters of N-protected (4S)-3-oxo-4-amino-butanoic acid derivatives of general formula:

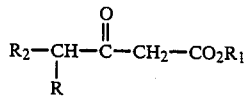

in which R, $R_1$ and $R_2$ have the same meaning as above.

Such an ether/aprotic solvent mixture is particularly well suited for the preparation of the compounds of formula IV in which $R_1$ represents methyl and $R_2$ represents isobutyl and more particularly for the preparation of methyl(4S)-3-oxo-4-amino-6-methyl-heptanoate.

In this case, a tetrahydrofuran/dimethylsulphoxide mixture is preferable as such a mixture provides yields of the desired product in pure form which are often above 60% whereas in tetrahydrofuran alone yields are only 25 to 30%.

The alkali metal salt of formula I—I' is then formed by reacting the butanoate derivatives of formula IV, in aqueous medium, with an alkali metal hydroxide at a temperature inferior to 20° C. and the salt so formed is subsequently separated from the reaction medium.

The compounds of formula II can be prepared from a N-protected amino acid of general formula:

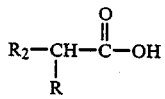

in which R and $R_2$ have the same meaning as above, and N,N-thionyldiimidazole following a method similar to that described in Bull. Soc. Chim. France 1964, pp. 945–951.

The compounds of formula V are either known products or products which can be prepared by protecting, following a classical procedure, the amino and optionally the mercapto groups of the corresponding L-amino acids. These amino acids are known natural products or compounds similar to these products. Such amino acids as well as their preparation are described in Belgian Patents Nos. 833,640 or 845,187.

The alkali metal salts of the invention so obtained can be used in particular for regenerating the esters of the corresponding N-protected (4S)-3-oxo-4-amino-butanoic acid derivatives by acidification with a strong acid such as hydrochloric acid.

In this application, the intermediate separation out of the alkali metal salts of the invention constitutes a method of choice for the purification of the esters of the N-protected (4S)-3-oxo-4-amino-butanoic acid derivatives of formula IV obtained in crude form when the above-described process of preparation is applied.

Therefore, another object of the invention relates to the use of the butanoic acid derivatives of formula I—I' for purifying the esters of the corresponding N-protected (4S)-3-oxo-4-amino-butanoic acid derivatives, obtainedin crude form, which consists in forming, by means of an alkali metal hydroxide the alkali metal salt of the esters of the corresponding N-protected (4S)-3-oxo-4-amino-butanoic acid derivatives in question, isolating the salt formed and then regenerating the esters N-protected(4)-3-oxo-4-amino-butanoic acid derivatives by acidification with a strong acid.

This purification through the corresponding alkali metal salt provides the esters of N-protected (4S)-3-oxo-4-amino-butanoic acid derivatives in high yields. In the case of lower alkyl(4S)-3-oxo-4-amino-6-methyl-heptanoates, yields were found superior to 60% calculated from N-protected L-leucine. Thus, the purification of the compounds of formula IV using the intermediate step of formation of the isolated alkali metal salts represents an undeniable advantage over the fractional crystallisation which is the prior-art method. The esters of the N-protected (4S)-3-oxo-4-amino-butanoic acid derivatives so purified will subsequently provide, after reduction, for example by catalytic hydrogenation, esters of N-protected (3S,4S; 3R,4S)-3-hydroxy-4-amino-butanoic acid derivatives in the form of a diastereoisomer mixture practically free from undesirable by-products.

At this stage, the separation of the two diastereoisomers, for instance by chromatography can be undertaken with a practically quantitative yield.

It has, furthermore, been observed that the preparation of the esters of N-protected (3S,4S; 3R,4S)-3-hydroxy-4-amino-butanoic acid derivatives can be directly carried out from the salts of formula I—I', by raducing these compounds for example by catalytic hydrogenation.

In this manner, one process step can be avoided namely the regeneration of the esters of N-protected (4S)-3-oxo-4-amino-butanoic acid derivatives from their alkali metal salts.

Thus, another object of the invention relates to a method of use of the butanoic acid derivatives of formula I—I' for preparing the (3S,4S) and (3R,4S) diastereoisomers of the esters of the corresponding N-protected 3-hydroxy-4-amino-butanoic acid derivatives which consist in reducing the compounds of formula I—I', for instance by catalytic hydrogenation, to obtain the esters of N-protected (3S,4S; 3R,4S)-3-hydroxy-4-amino-butanoic acid derivatives in the form of mixtures of diastereoisomers then separating the diastereoisomers in question, for example by chromatography.

The yields registered when this alternative procedure is used are similar to those obtained when reducing the esters of N-protectsd (4S)-3-oxo-4-amino-butanoic acid derivatives purified through the intermediate formation of the alkali metal salt, namely superior to 90% in the case of N-protected lower alkyl (4S)-3-oxo-4-amino-6-methyl-heptanoates.

Therefore, undeniable improvements to the known procedures for preparing esters of N-protected 3-hydroxy-4-amino-butanoic acid derivatives are provided by the alkali metal salts of the invention when operations on the industrial scale are undertaken.

The non-limitative Examples which follow illustrate the invention.

MODES OF PREPARATION

(A) N,N-thionyldiimidazole

Into a 1l-flask fitted with a stirrer and a dropping-funnel closed with a drying-trap, were introduced 13.6 g (0.2 mol) of imidazole dissolved in 150 ml of tetrahydrofuran.

While stirring, there was then added a solution of 6 g of thionylchloride in 50 ml of tetrahydrofuran.

Precipitation of the imidazole hydrochloride started immediately. After stirring for 20 minutes, the precipitate was filtered out and washed with 50 ml of tetrahydrofuran. In this manner, there was obtained a clear solution of N,N-thionyldiimidazole which was used as such in the following operation.

(B) N-BOC-L-leucine imidazolide

Into a 1l-flask fitted with a stirrer and a dropping-funnel, the solution previously obtained was introduced and then a solution of 11.5 g (0.05 mol) of N-BOC-L-leucine in 20 ml of tetrahydrofuran was added drop-by-drop.

Stirring was maintained for 20 minutes and the sulphurous anhydride so formed was eliminated by suction under vacuum (about 20 mm Hg). In this manner, a slightly cloudy solution of N-BOC-L-leucine imidazolide was obtained which was used in crude form.

(C) Methyl acid malonate

Into a 4l-flask fitted with a stirrer and a dropping-funnel were placed 660 g (5 mols) of dimethyl malonate. There was then added over a period of about 8 hours a solution at 20° C. of 281 g of potassium hydroxide in 2 l of methanol. After stirring for 15 to 16 hours at room-temperature, the precipitate of potassium salt of methyl acid malonate was filtered out, and carefully washed with ethyl ether.

The precipitate was taken up in 750 ml of water and acidified with dilute hydrochloric acid to pH=2 to 3 while being cooled with an ice/methanol mixture. The medium was extracted 3 times with ethyl ether and the ethereal phase was dried and evaporated to dryness.

In this manner, 156 g of crude methyl acid malonate were obtained, which represents a yield of 26%.

After distillating under $5.10^{-2}$ Torr at 80°-85° C., 135 g of pure product were isolated which represents a yield of 23%.

$n_D^{23} = 1,4300$

N.M.R.: (nuclear magnetic resonnance): conforms
Protometric titration: 97.17%

Following the same method but starting from diethyl malonate, ethyl acid malonate was prepared.

(D) Magnesium enolate of methyl acid malonate

Into a 2l-flask fitted with a stirrer, a condenser and a dropping-funnel were successively introduced 4.8 g (0.2 mol) of magnesium, 0.2 ml of carbon tetrachloride and 10 ml of methanol.

To this mixture, were added, under stirring, 10 ml of a solution of 23.5 g (0.2 mol) of methyl acid malonate in 50 ml of methanol.

The reaction started immediately. When it became less violent, the remainder of the malonate solution was added so as to maintain mild reflux. When this operation was terminated, the medium was heated on a water-bath for 8 hours and 200 ml of tetrahydrofuran were then added. Heating on the water-bath was maintained for 12 hours. The solvents were distilled off, first under atmospheric pressure and then under about 20 mm Hg. When dryness was obtained, 100 ml of benzene were added and the mixture was distilled first at atmospheric pressure and then under vacuum.

Finally, 100 ml of tetrahydrofuran were added. In this manner, a suspension of magnesium enolate of methyl acid malonate was obtained.

Using the same procedure but starting from ethyl acid malonate, magnesium enolate of ethyl acid malonate was obtained.

EXAMPLE

Preparation of methyl (4S)-3-oxo-4-N-BOC-amino-6-methyl-heptanoate, sodium salt.

N-BOC-L-leucine imidazolide was prepared from 13.6 g of imidazole and 11.5 g of N-BOC-L-leucine following the method described in paragraph B above. Likewise, the magnesium enolate of methyl acid malonate was prepared from 24.7 g of methyl acid malonate following the method described in paragraph D above.

The imidazolide solution was added to the magnesium enolate suspension in tetrahydrofuran and then 130ml of dimethylsulphoxide were added. The mixture became clear and was completely dissolved.

After stirring for 4 hours at room-temperature, the medium was acidified by means of 1M-hydrochloric acid to neutral pH and stirring was maintained for 30 minutes at room-temperature to complete the hydrolysis.

The mixture was decanted and extracted 3 times with ethyl ether. The ethereal phase was then washed successively with water, bicarbonated water and again with water. After drying on sodium sulphate, the medium was evaporated to dryness to provide 12.2 g of crude methyl (4S)-3-oxo-4-N-BOC-amino-6-methyl-heptanoate (Yield: 86%).

The crude methyl heptanoate derivative was taken up in 60 ml of hexane and 20 ml of water. The heterogenous mixture was stirred and 10 ml of a 30%-sodium hydroxide solution were added at a temperature below 20° C. The precipitation of the sodium salt started after about 5 minutes. To complete the precipitation, stirring was maintained for 15 minutes.

The precipitate was filtered out and washed with iced water and ethyl ether. After drying, 9.5 g of the sodium salt of methyl (4S)-3-oxo-4-N-BOC-amino- 6-methyl-heptanoate, were obtained which were slightly soluble in ethyl ether.

Yield: 62% calculated from N-BOC-L-leucine
M.P.: 187° C. (decomposition)
Analysis $C_{14}H_{24}NO_5Na$ Calculated C: 54.36%; H: 7.82%; N: 4.53%; Found C: 54.22%; H: 7.90%; N: 4.70%.

Acidobasic determination: 100.6%
$\alpha_D^{25} = -1.79°$ (C=1, methanol)
N.M.R. and T.L.C. (thin layer chromatography): conforms Using the same method as that described above, the following compounds were prepared:
Methyl(4S)-3-oxo-4-N-BOC-amino-5-phenyl-pentanoate, sodium salt M.P.: 195°-197° C.
Methyl (4S)-3-oxo-4-N-BOC-amino-5-cyclohexyl-pentanoate, sodium salt M.P.: 120°-122° C.
Methyl (4S)-3-oxo-4-N-BOC-amino-4-phenyl-butyrate, sodium salt M.P.: 182°-184° C.
Methyl (4S)-3-oxo-4-N-BOC-amino-5-methyl-hexanoate, sodium salt Soluble in water
Methyl (4S)-3-oxo-4-N-BOC-amino-octanoate, sodium salt M.P.: 200°-202° C.
Methyl (4S)-3-oxo-4-N-BOC-amino-pentanoate, sodium salt $\alpha_D^{21} = -10.0°$ (C=1, methanol)
Methyl (4S)-3-oxo-4-N-BOC-amino-hexanoate, sodium salt
Methyl (4S)-3-oxo-4-N-BOC-amino-4-cyclohexyl-butyrate, sodium salt Methyl (4S)-3-oxo-4-N-BOC-amino-5-(4-hydroxyphenyl)-pentanoate, sodium salt Methyl (4S)-3-oxo-4-N-BOC-amino-5-(1H-imidazol-4-yl)-pentanoate, sodium salt

EXAMPLE 2

Preparation of ethyl (4S)-3-oxo-4-N-BOC-amino-6-methyl-heptanoate, sodium salt

In a 2l-flask there was stirred a mixture of N-BOC-L-leucine imidazolide (prepared from 77 g of imidazole and 65.5 g (0.28 mol) of anhydrous N-BOC-L-leucine following the method described in the above paragraph B) and of magnesium enolate of ethyl acid malonate (prepared from 151 g of ethyl acid malonate following the method described in the above paragraph D).

After this operation, the suspension was acidified with 1M-hydrochloric acid to neutral pH. Stirring was maintained for 30 minutes at room-temperature to complete the hydrolysis. After decantation, the ethereal phase was extracted three times with ethyl ether and washed successively with water, bicarbonated water and again with water. After drying on sodium sulphate, the medium was evaporated to dryness to provide ethyl (4S)-3-oxo-4-N-BOC-amino-6-methyl-heptanoate in crude form. The crude ethyl heptanoate derivative was taken up in 60 ml of ethyl ether and 60 ml of water. The heterogenous mixture was stirred and 30 ml of a 30%-sodium hydroxide solution was added at a temperature below 20° C.

Stirring was maintained for 15 to 20 minutes and the precipitate formed was filtered out and washed with iced water and ethyl ether.

After drying, 56.5 g of ethyl (4S)-3-oxo-4-N-BOC-amino-6-methyl-heptanoate, sodium salt were obtained.

Yield: 62.2% calculated from N-BOC-L-leucine
M.P.: 180° C. (decomposition)

The following Examples illustrate the use of the compounds of the invention:

EXAMPLE I

Preparation of methyl (4S)-3-oxo-4-N-BOC-amino-6-methyl-heptanoate.

The N-BOC-L-leucine imidazolide was prepared from 136 g of imidazole and 115 g of N-BOC-L-leucine following the method described in paragraph B above. Similarly, the magnesium enolate of methyl acid malonate was prepared from 236 g of methyl acid malonate following the method described in paragraph D above.

The solution of imidazolide was added to the suspension of magnesium enolate in tetrahydrofuran and 1.3 l of dimethylsulphoxide was added.

The mixture became clear and was completely dissolved.

After stirring for 4 hours at room-temperature, 1M-hydrochloric acid was added to neutral pH. Stirring was maintained for 30 minutes at room-temperature to complete the hydrolysis. After decantation, the ethereal phase was extracted three times with ethyl ether and successively washed with water, bicarbonated water and again with water.

After drying on sodium sulphate and evaporation to dryness there were obtained 129 g of crude methyl (4S)-3-oxo-4-N-BOC-amino-6-methyl-heptanoate (yield: 89%)

The crude methyl heptanoate derivative was taken up in 200 ml of isopropyl ether, 200 ml of hexane and 100 ml of water.

At a temperature below 20° C., 50 ml of 30%-sodium hydroxide were then added while stirring. After stirring for 15 minutes, the precipitate of methyl (4S)-3-oxo-4-N-BOC-JbNsino-6-methyl-heptanoate, sodium salt so formed was filtered out and washed with hexane.

The wet precipitate was taken up in a water/hexane mixture and 1M-hydrochloric acid was added to pH=2 to 3.

Extraction was performed twice with hexane and the organic layer was washed with a 10%-sodium bicarbonate solution. After drying and evaporating, 86.2 g of methyl (4S)-3-oxo-4-N-BOC-amino-6-methyl-heptanoate were obtained in oily form.

Yield: 62% calculated from N-BOC-L-leucine.
$\alpha_D^{25} = -55.1°$ (C=1, methanol)
N.M.R. and T.L.C.: conforms Using the same method as that described above, the following compounds were prepared, the yields being calculated from the corresponding N-BOC-L-amino acid.

Methyl (4S)-3-oxo-4-N-BOC-amino-5-phenyl-pentanoate Yield: 51% M.P.: 85°-86° C. (hexane)
$\alpha_D^{25} = -60.4°$ (C=1, methanol)

Methyl (4S)-3-oxo-4-N-BOC-amino-5-cyclohexyl-pentanoate. Yield: 76% Oily
$\alpha_D^{25} = -34.3°$ (C=1, methanol)

Methyl (4S)-3-oxo-4-N-BOC-amino-4-phenyl-butyrate Yield: 52%
M.P.: 97°-98° C. (toluene)
$\alpha_D^{25} = +77°$ (C=1, methanol)

Methyl (4S)-3-oxo-4-N-BOC-amino-5-methyl-hexanoate
Yield: 75% Oily
$\alpha_D^{25} = -43.4°$ (C=1, methanol)

Methyl (4S)-3-oxo-4-N-BOC-amino-octanoate
Yield: 59% M.P.: 47°-48° C. (n-pentane)
$\alpha_D^{25} = -45.7°$ (C=1, methanol)

Methyl (4S)-3-oxo-4-N-BOC-amino-pentanoate
Yield: 75%
$\alpha_D^{21} = -52.6°$ (C=1, methanol)

Methyl (4S)-3-oxo-4-N-BOC-amino-5-(3-indolyl)-pentanoate Yield: 74%
$\alpha_D^{21} = -34.1°$ (C=1, methanol)

EXAMPLE II

Preparation of methyl (4S)-3-oxo-4-N-BOC-amino-6-methyl-heptanoate

To the suspension of magnesium enolate of methyl acid malonate obtained in paragraph D above (prepared from 23.5 g of methyl acid malonate), was added, at room-temperature and under stirring, the solution of imidazolide obtained in paragraph B above (prepared from 11.5 g of N-BOC-L-leucine).

A suspension was obtained into which 300 ml of anhydrous direthylsulphoxide were added while stirring. Complete dissolution was then observed.

After stirring for 4 hours at room-temperature, hydrolysis was carried out with 1M-hydrochloric acid at 20° C. (pH=5 to 6). Stirring was maintained for 30 minutes to complete the hydrolysis. After decantation, the organic phase was extracted three times with hexane and then washed successively with water, bicarbonated water and again with water. After drying on sodium sulphate and evaporation to dryness, 26 g of crude methyl (4S)-3-oxo-4-N-BOC-amino-6-methyl-heptanoate were obtained in oily form (yield: 90%). This crude methyl heptanoate derivative was taken up in 100 ml of isopropyl ether, 200 ml of hexane and 100 ml of water. At a temperature below 20° C., 50 ml of a 30%-sodium hydroxide solution were added while stirring. After stirring for a further 15 minutes, the precipitate of methyl (4S)-3-oxo-4-N-BOC-amino-6-methyl-heptanoate, sodium salt was filtered out and washed with hexane.

The wet precipitate was taken up in a water/hexane mixture and 1M-hydrochloric acid was added to pH=2 to 3.

The medium was twice extracted with hexane and the organic phase was washed with a 10%-sodium bicarbonate solution. After drying and evaporating, 18 g of methyl (4S)-3-oxo-4-N-BOC-amino-6-methyl-heptanoate were obtained in oily form which solidified on standing.

Yield: 63% calculated from N-BOC-L-leucine M.P.: 32°–34° C. (pentane at about −30° C.)

$\alpha_D{}^{25} = -55.1°$ (C=1, methanol)

N.M.R. and T.L.C.: conforms

Using the same procedure as that described above but replacing dimethyl-sulphoxide by N,N-dimethylformamide, methyl (4S)-3-oxo-4-N-BOC-amino-6-methyl-heptanoate was obtained in a yield of 53%.

EXAMPLE III

Preparation of methyl (4S)-3-oxo-4-N-BOC-amino-6-methyl-heptanoate

The 9.5 g of methyl (4S)-3-oxo-4-N-BOC-amino-6-methyl-heptanoate, sodium salt obtained in Example 1 were dissolved in water and 1M-hydrochloric acid was added to pH=2 to 3. The medium was twice extracted with hexane and the organic phase was washed with a 10%-sodium bicarbonate solution. After drying and evaporating, 8.5 g of pure methyl (4S)-3-oxo-4-N-BOC-amino-6-methyl-heptanoate were isolated.

Yield: 96% calculated from the sodium salt or 60% calculated from N-BOC-L-leucine.

Using the same procedure as that described above but starting from the 56.5 g of the sodium salt of ethyl (4S)-3-oxo-4-N-BOC-amino-6-methyl-heptanoate prepared in Example 1, 47.4 g of ethyl (4S)-3-oxo-4-N-BOC-amino-6-methylheptanoate were obtained.

Yield: 90% calculated from the sodium salt or 56% calculated from N-BOC-L-leucine.

EXAMPLE IV

Preparation of methyl (4S)-3-hydroxy-4-N-BOC-amino-6-methyl-heptanoate

In 400 ml of anhydrous methanol were dissolved the 86.2 g of pure methyl (4S)-3-oxo-4-N-BOC-amino-6-methyl-heptanoate obtained from its sodium salt as described in Example I. After 6 g of Raney's nickel had been added, hydrogenation was performed for 72 hours under a pressure of about 7 kg and at a temperature of about 20° C.

After this operation, the medium was filtered and evaporated to dryness to obtain 81.7 g of a mixture of two (3S,4S; 3R,4S) diastereoisomers of methyl 3-hydroxy-4-N-BOC-amino-6-methyl-heptanoate in oily form (yield: 94% from the 3-oxo derivative or 58.2% from N-BOC-L-leucine).

This oil was then separated by chromatography on a silica gel column (diameter: 90 mm, height: 500 mm) using an ethyl acetate/hexane 10:90 mixture.

After the different fractions had been evaporated off, the two diastereoisomers, which crystallised on standing, were isolated. Thus, the following were obtained:

(a) 30.8 g of (3S,4S)isomer

Yield: 37% calculated from the 3-oxo derivative M.P.: 59° C.

$\alpha_D{}^{25} = -39.5°$ (C=1, methanol)

N.M.R.: conforms (b) 48.1 g of (3R,4S)isomer

Yield: 58.8% calculated from the 3-oxo derivative M.P.: 63.5° C.

$\alpha_D{}^{25} = -23.5°$ (C=1, methanol)

N.M.R.: conforms

EXAMPLE V

Preparation of methyl (3S,4S)-3-hydroxy-4-N-BOC-amino-6-methyl-heptanoate

In 150 ml of methanol there were dissolved 6 g of the sodium salt of methyl (4S)-3-oxo-4-N-BOC-amino-6-methyl-heptanoate. After 1 g of Raney's nickel had been added, hydrogenation was performed under a pressure of 7 kg for 24 hours.

Alkalinity was neutralised by adding acetic acid and the medium was filtered. After evaporation, the medium was taken up in hexane to eliminate the mineral salts. The hexane was evaporated off and 5.3 g were obtained of a mixture of two (3S,4S; 3R,4S) diastereoisomers of crude methyl 3-hydroxy-4-N-BOC-amino-6-methyl-heptanoate (yield: 91% from the sodium salt or 56.4% from N-BOC-L-leucine). This crude mixture was then separated by chromatography on a silica column (diameter: 90 mm, height: 500 mm) using an ethyl acetate/hexane 10:90 mixture.

After the different fractions were evaporated, the two diastereoisomers which cristallised on standing, were isolated. In this way, the following were obtained:

(a) 1.73 g of (3S, 4S)isomer

Yield: 30% calculated from the sodium salt M.P.: 59° C.

$\alpha_D{}^{25} = -36.3°$ (C=1, methanol)

T.L.C.: conforms (b) 3.2 g of (3R,4S)isomer

Yield: 55% M.P.: 63° C.

$\alpha_D{}^{25} = -21.85°$ (C=1, methanol)

Using the same method as that described above, the following compounds were prepared, the yields being calculated from the corresponding (4S)-3-oxo-4-N-BOC-amino derivative.

Methyl (3S,4S)-3-hydroxy-4-N-BOC-amino-5-phenyl-pentanoate. Yield: 20% M.P.: 96°–97° C. (n-pentane)

$\alpha_D{}^{25} = -34.9°$ (C=1, methanol)

Methyl (3R,4S)-3-hydroxy-4-N-BOC-amino-5-phenyl-pentanoate Yield: 30% M.P.: 130°–131° C. (n-pentane)

$\alpha_D{}^{25} = -16.9°$ (C=1, methanol)

Methyl (3S,4S)-3-hydroxy-4-N-BOC-amino-5-cyclohexyl-pentanoate Yield: 15% M.P.: 65°–66° C. (n-pentane)

$\alpha_D{}^{25} = -32.8°$ (C=1, methanol) Methyl (3R,4S)-3-hydroxy-4-N-BOC-amino-5-cyclohexyl-pentanoate Yield: 22% M.P.: 81°–82° C. (n-pentane)

$\alpha_D{}^{25} = -22.2°$ (C=1, methanol)

Methyl (3S,4S)-3-hydroxy-4-N-BOC-amino-4-phenyl-butyrate. Yield: 12% M.P.: 94°–95° C. (diisopropyl ether) $\alpha_D{}^{25} = +7.9°$ (C=1, methanol)

Methyl (3R,4S)-3-hydroxy-4-N-BOC-amino-4-phenyl-butyrate Yield: 45% M.P.: 94°–95° C. (diisopropyl ether)
$\alpha_D{}^{25} = +1.8°$ (C=1, methanol)

Methyl (3S,4S)-3-hydroxy-4-N-BOC-amino-5-methyl-hexanoate Yield: 22% M.P.: 58°–59° C. (n-pentane)
$\alpha_D{}^{25} = -43.85°$ (C=1, methanol)

Methyl (3R,4S)-3-hydroxy-4-N-BOC-amino-5-methyl-hexanoate Yield: 44% M.P.: 64°–65° C. (n-pentane)
$\alpha_D{}^{25} = -11.25°$ (C=1, methanol)

Methyl (3S,4S)-3-hydroxy-4-N-BOC-amino-octanoate Yield: 35% M.P.: 54°–55° C. (n-pentane)
$\alpha_D{}^{25} = -15.4°$ (C=1, methanol)

Methyl (3R,4S)-3-hydroxy-4-N-BOC-amino-octanoate Yield: 38% M.P.: 78°–79° C. (n-pentane)
$\alpha_D{}^{25} = -15.4°$ (C=1, methanol)

EXAMPLE VI

Preparation of ethyl (3S,4S)-3-hydroxy-4-N-BOC-amino-6-methyl-heptanoate

In 80 ml of anhydrous methanol there were dissolved 8.3 g of pure ethyl (4S)-3-oxo-4-N-BOC-amino-6-methyl-heptanoate obtained from its sodium salt as described in Example II. After about 1 g of Raney's nickel had been added, the medium was hydrogenated for 48 hours under a pressure of 7 kg. After this operation, the medium was filtered and evaporated to dryness to obtain a mixture of two (3S,4S ; 3R,4S) diastereoisomers of ethyl 3-hydroxy-4-N-BOC-amino-6-methyl-heptanoate in a yield of 90%.

This oil was separated by chromatography on a silica gel column (diameter: 90 mm, height: 500 mm) using an ethyl acetate/hexane 10:90 mixture.

After the different fractions had been evaporated off, the two diastereoisomers were isolated in oily form. In this way, the following were obtained:

(a) 3.3 g of (3S,4S)isomer
Yield: 40% calculated from ethyl (4S)-3-oxo-4-N-BOC-amino-6-methyl-heptanoate
$\alpha_D{}^{25} = -31.7°$ (C=1, methanol)
N.M.R. and T.L.C.: conforms (b) 4.1 g of (3R,4S)isomer
Yield: 50% calculated from ethyl (4S)-3-oxo-4-N-BOC-amino-6-methyl-heptanoate
$\alpha_D{}^{25} = -14.7°$ (C=1, methanol)
N.M.R. and T.L.C.: conforms

We claim:

1. A 4-amino-butanoic acid derivative of formula:

in which:

M represents an alkali metal atom;

R represents a phthalimido group or an amino group protected by a formyl, acetyl, propionyl, tert-butoxycarbonyl, methoxyacetyl, methoxypropionyl, 2,2,2,-trichloroethyloxycarbonyl, benzyloxycarbonyl, p-nitrobenzyloxycarbonyl, trityl, methoxytrityl or p-toluenesulfonyl group;

$R_1$ represents a lower alkyl group, a benzyl or xylyl group;

$R_2$ represents hydrogen, a branched- or straight-chain alkyl radical having from 1 to 6 carbon; Cy-A, wherein Cy is phenyl, hydroxyphenyl, methylphenyl, mono-fluorophenyl, mono-chlorophenyl, mono-bromophenyl, di-fluorophenyl, di-chlorophenyl, di-bromophenyl, mono-methoxyphenyl, di-methoxyphenyl, tri-methoxyphenyl, trifluoromethylphenyl or nitrophenyl; naphthyl or $C_{3-7}$ cycloalkyl; and A represent a single bond or a branched- or straight-chain alkylene radical having from 1 to 5 carbon atoms.

2. A 4-amino-butanoic acid derivative according to claim 1 in which $R_2$ represents methyl, ethyl, n-propyl, isopropyl, n-butyl, isobutyl, tert-butyl, 1-methyl-propyl, n-pentyl, n-hexyl, phenyl, hydroxyphenyl, methylphenyl, mono-fluoro-phenyl, mono-chloro-phenyl, mono-bromo-phenyl, di-fluoro-phenyl, di-chloro-phenyl, di-bromo-phenyl, mono-methoxy-phenyl, di-methoxy-phenyl, tri-methoxy-phenyl, trifluoromethyl-phenyl or nitrophenyl.

3. A 4-amino-butanoic acid derivative according to claim 1 in which $R_2$ represents methyl.

4. A 4-amino-butanoic acid derivative according to claim 1 in which $R_2$ represents ethyl.

5. A 4-amino-butanoic acid derivative according to claim 1 in which $R_2$ represents n-propyl.

6. A 4-amino-butanoic acid derivative according to claim 1 in which $R_2$ represents isopropyl.

7. A 4-amino-butanoic acid derivative according to claim 1 in which $R_2$ represents n-butyl.

8. A 4-amino-butanoic acid derivative according to claim 1 in which $R_2$ represents isobutyl.

9. A 4-amino-butanoic acid derivative according to claim 1 in which $R_2$ represents 1-methyl-propyl.

10. A 4-amino-butanoic acid derivative according to claim 1 in which $R_2$ represents phenyl.

11. A 4-amino-butanoic acid derivative according to claim 1 in which $R_2$ represents 4-hydroxy-phenyl.

12. A 4-amino-butanoic acid derivative according to claim 1 in which $R_2$ represents cyclohexyl.

13. A 4-amino-butanoic acid derivative according to claim 1 in which $R_1$ represents methyl, ethyl, n-propyl, isopropyl, n-butyl, isobutyl, tert-butyl, benzyl or xylyl.

14. A 4-amino-butanoic acid derivative according to claim 1 in which M represents sodium.

15. A alkali metal salt of a lower alkyl N-protected (4S)-3-oxo-4-amino-6-methyl-heptanoates.

16. An alkali metal salt according to claim 15 wherein the lower alkyl group is methyl or ethyl and the N-protecting group is t-butoxycarbonyl.

17. An alkali metal salt according to claim 16, wherein the alkali metal is sodium.

18. An alkali metal salt as claimed in claim 17 which is in substantially pure crystalline form.

* * * * *